United States Patent
Aufaure et al.

[19]

[11] Patent Number: 6,022,365
[45] Date of Patent: Feb. 8, 2000

[54] MICROKERATOME FOR OPHTHALMOLOGICAL SURGERY

[75] Inventors: Jean-Luc Aufaure, Souvigny; Alain Duprat, Roquettes, both of France

[73] Assignee: Moria SA, Antony, France

[21] Appl. No.: 09/145,967

[22] Filed: Sep. 3, 1998

[30] Foreign Application Priority Data

Sep. 4, 1997 [FR] France ................................. 97 11010

[51] Int. Cl.⁷ ............................................... A61F 9/00
[52] U.S. Cl. ............................................................. 606/166
[58] Field of Search ............................ 606/4, 166, 5, 606/161

[56] References Cited

U.S. PATENT DOCUMENTS 4,662,370  5/1987  Hoffmann et al. ..................... 606/166
5,342,778  8/1994  Giraud et al. .
5,586,980  12/1996  Kremer et al. .
5,624,456  4/1997  Hellenkamp .
5,807,380  9/1998  Dishler .................................... 606/166

FOREIGN PATENT DOCUMENTS 0771553  5/1997  European Pat. Off. .

*Primary Examiner*—Michael Buiz
*Assistant Examiner*—Kevin Truone
*Attorney, Agent, or Firm*—Griffin, Butler, Whisenhunt & Szipl, LLP

[57] ABSTRACT

Microkeratome for surgery of the cornea, comprising a securing ring (1) which includes, on an upper surface, a slide (8), and a blade carriage (10) equipped in the lower part with guide means (13) for cooperating with the slide (8), the ring including a maneuvering grip, the blade carriage (10) including a front section (12) forming a plateau (16) for flattening the cornea, in which the ring (1) and the carriage (10) include abutments (17, 18) for regulating the end of slide position of the carriage (10) in relation to the ring (1).

8 Claims, 2 Drawing Sheets

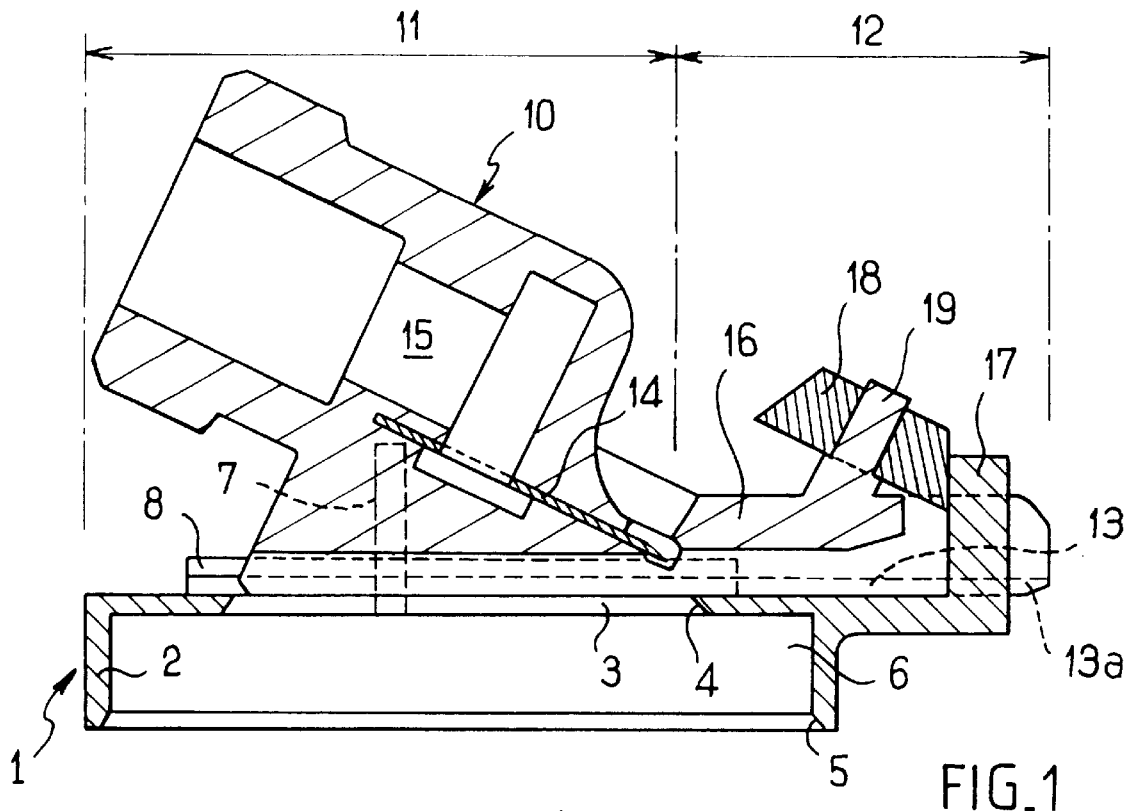
FIG_1
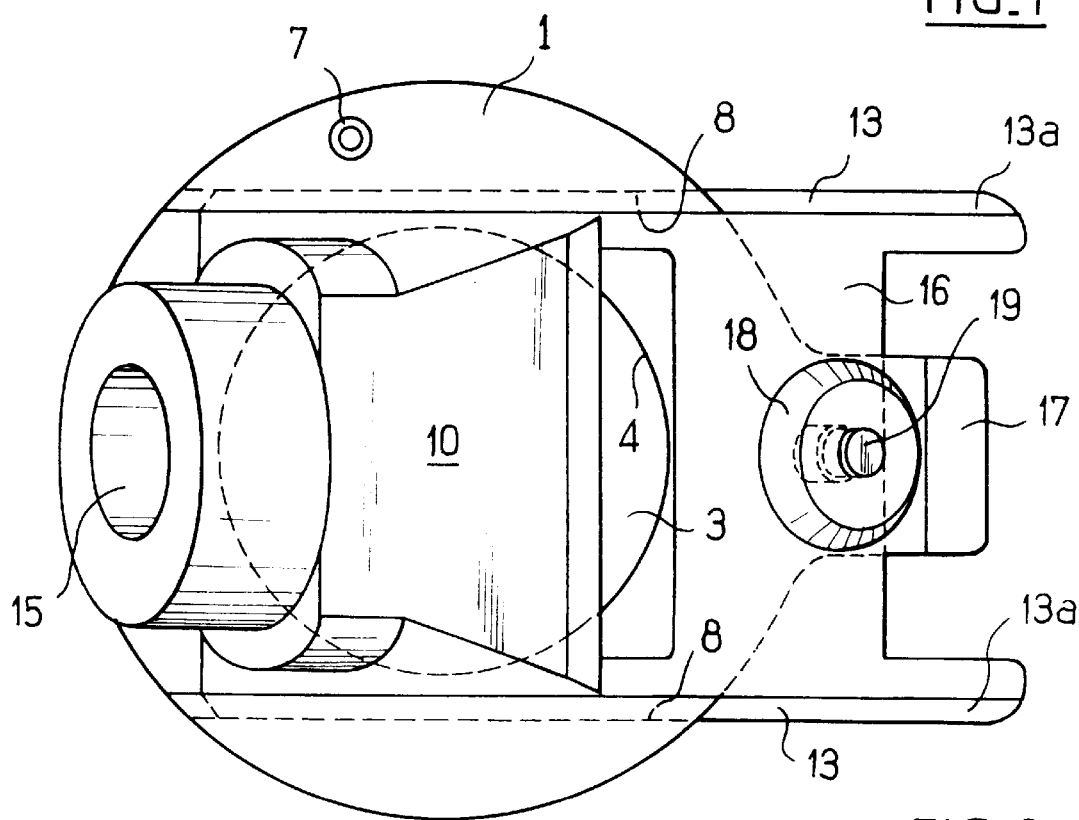
FIG_2

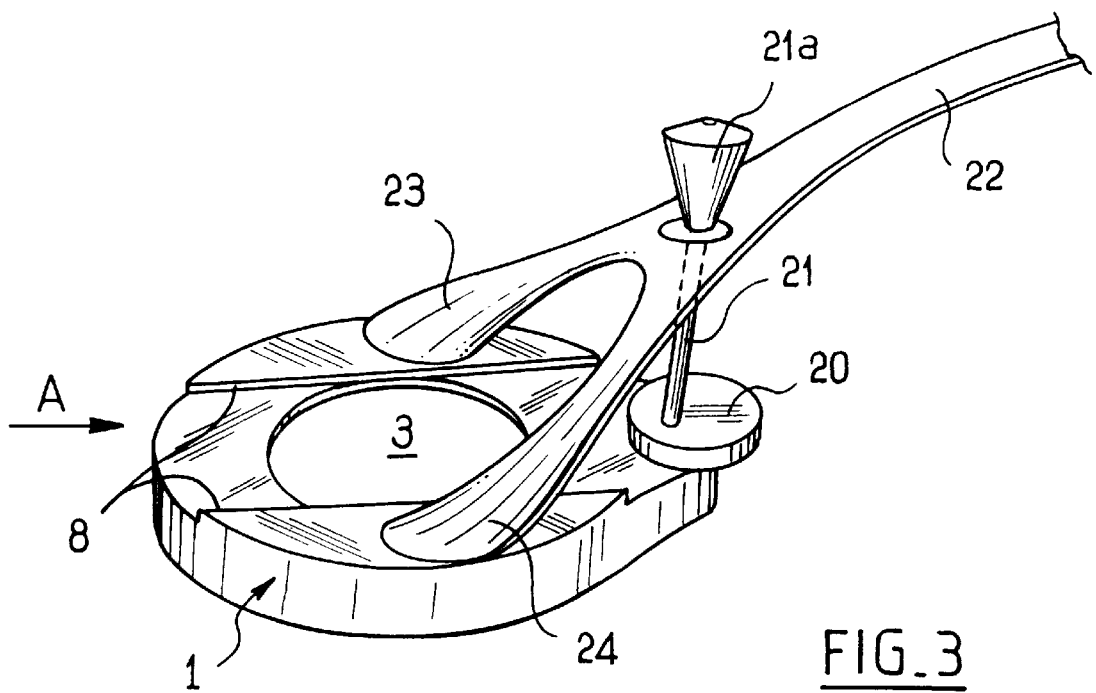
FIG_3
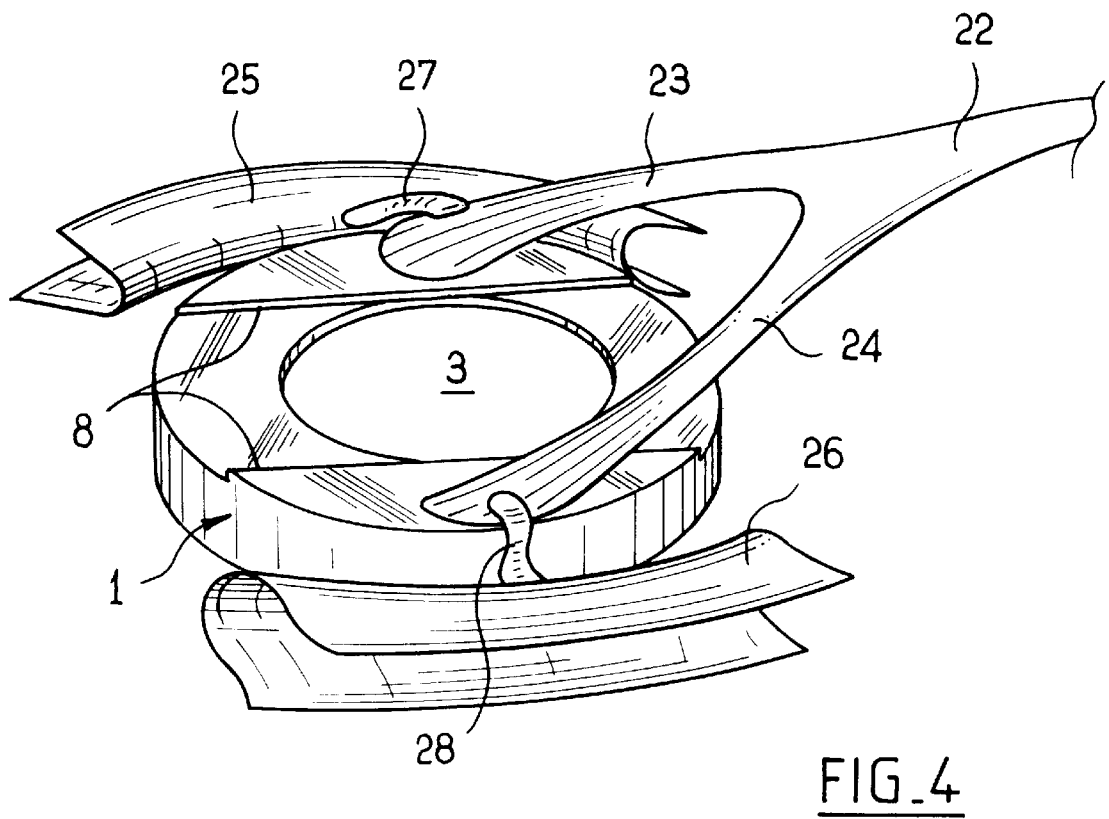
FIG_4

MICROKERATOME FOR OPHTHALMOLOGICAL SURGERY

FIELD OF THE INVENTION

The present invention concerns the field of surgical instruments intended in particular for ophthalmology.

PRIOR ART

Among the techniques used in refractive surgery (corneal surgery) aimed at correcting an ametropia, there is a technique developed by Professor Barraquer called "in situ keratomileusis". This technique consists in removing a pellicular part of the cornea by cutting a flap in the cornea. With this flap removed, the surgeon then proceeds to withdraw a lenticule from the plane exposed by the withdrawal of the flap, the thickness and dimensions of which lenticule are a function of the correction which is to be made. The corneal flap is then put back in place on the plane thus modified, which translates into a modification in the external refractive surface of the eye.

Today, this technique is once again attracting interest through the use of photorefractive surgery. The reason is that because this surgery allows extremely precise ablations to be performed by means of a laser, it has become possible to control the dimensions of the lenticules much more finely than with the mechanical ablation means which have been used hitherto.

Thus, in this type of intervention, the corneal flap is removed using a microkeratome, that is to say an instrument akin to a miniaturized plane with a blade vibrating in the direction of its cutting edge, the cutting depth of which is regulated by means of wedges of precalibrated thickness or micrometer screws.

Photorefractive surgery has made it possible to simplify these microkeratomes by imposing, over the course of time, a substantially constant thickness of the corneal flap. The "cutting depth" having become constant, the microkeratome has lost some of its adjustment members and in particular the calibrated wedges or screws used for regulating the thickness of the corneal flap to be removed.

A microkeratome has recently been proposed in which the number of components used is reduced in order to simplify its production and in particular the preparation before each intervention.

The fact remains that the microkeratome is still today a miniaturized instrument whose manual manipulation is tricky. The object of the present invention is to improve the safety of the operation by increasing the comfort of the surgeon by virtue of an instrument equipped with means for improving the operating field of vision at the same time as the holding and maneuvering of the instrument.

SUMMARY OF THE INVENTION

To this end, the invention therefore relates to a microkeratome for surgery of the cornea, comprising a securing ring which includes a slide on an upper surface, and a blade carriage equipped in the lower part with guide means for cooperating with the slide, the ring including a maneuvering grip, the blade carriage including a front section forming a plateau for flattening the cornea, in which the ring and the carriage include abutments for regulating the end of slide position of the carriage in relation to the ring in the direction of cutting. The use of this abutment makes it possible to limit the cut of the corneal flap, which can thus remain attached to the eye via an uncut part, and to do this with certainty, whereas with the current microkeratomes the partial cutting of the corneal flap is dependent on the dexterity of the surgeon.

In a first embodiment, the abutment carried by the ring includes a lug rising above the plane of the slide. In this first embodiment, the abutment carried by the carriage includes a component of revolution carried movably on a finger rising above the plateau for flattening the cornea and forming a protrusion to the front of the plateau. Thus, by changing the dimension of this component of revolution, it is possible to vary the dimension of the portion of the corneal flap which remains attached to the eye.

In another embodiment, the abutment carried by the ring is a cam with adjustable positions. For example, this cam can be an eccentric whose side surface constitutes an abutment for the front part of the carriage, the position of which abutment in relation to the slide carried by the ring can be adjusted by rotating this eccentric.

In order to have a sufficient guide length between the carriage and the ring of the microkeratome, particularly in the first part of the cut, while at the same time retaining a dimension which is as compact as possible for the ring despite the use of the abovementioned abutments, the carriage includes two lower side rails for cooperating with the slide of the ring, the front end of the plateau being set back from the front end of the rails. This therefore gives a microkeratome whose plateau for flattening the cornea is of very short width in relation to the usual microkeratomes.

Moreover, in order to free as far as possible the operating field of vision of the surgeon and to make the instrument ergonomic, the maneuvering grip of the ring is in the shape of a fork whose prongs are implanted at an inclination in the ring on either side of the slide. Thus, the grip is oriented in the direction of the slide of the ring and the opposite way from the trajectory of the carriage when the corneal flap is being cut. The surgeon thus maneuvers the carriage with one hand in the direction of the grip which he is holding with the other hand in a mutually opposite manner so that when the carriage comes into abutment against the stop carried by the ring, the surgeon immediately senses this abutment via the grip and automatically compensates the force which the carriage applies to the ring, which would tend to tilt, and in extreme cases this could lead to rupturing of the suction attachment of the ring on the eye.

In order to further improve the comfort of the surgeon and thus the safety of the operation, the carriage of the microkeratome according to the invention will be made of a transparent material permitting a full view of the cut through the plateau for flattening the cornea. Finally, the ring for securing the microkeratome to the eye will advantageously be equipped externally with eye speculum elements. These elements normally belong to a separate mechanism whose structure necessarily obstructs the operating field of vision.

Other characteristics and advantages of the invention will be evident from the illustrative embodiments which are given in the description hereinafter by way of nonlimiting examples.

BRIEF DESCRIPTION OF THE DRAWINGS

Reference will be made to the attached drawings, in which:

FIG. 1 is a sectional view of a microkeratome according to the invention,

FIG. 2 is a plan view of FIG. 1,

FIG. 3 is a diagram of a securing ring belonging to the microkeratome according to the invention and equipped with a forked grip, FIG. 4 is a diagrammatic perspective view of a ring of the microkeratome according to the invention equipped with a forked grip and an eye speculum.

DESCRIPTION OF THE PREFERRED EMBODIMENTS

The microkeratome represented in FIGS. 1 and 2 includes, in a conventional manner, a ring 1 provided with a skirt 2 and an upper opening 3, the skirt and the upper opening defining circular spans 4 and 5 which rest on the eye in such a way that an annular chamber 6 is thus delimited and can be brought to partial vacuum by means of a connection piece 7 linked to a vacuum source (not shown). On either side of the opening 3, on its upper surface, the ring includes two slide faces 8 which define a slide in which a carriage 10 can be introduced and guided.

The carriage 10 includes, also in a conventional manner, two sections 11 and 12 bordered in the lower part by two guide rails 13 whose profile matches the profile of the slide faces 8. The rear section 11 is the section which carries a cutting blade 14 and its drive device (not shown) which is accommodated in a recess 15. It will be observed here, briefly, that this drive device is formed by an output shaft of a turbine which has, at its free end, an eccentric finger cooperating with a groove in a heel carrying the cutting blade 14 in order to transform the rotational movement of the output shaft of the turbine into a reciprocal movement of the cutting blade in a plane perpendicular to the plane of the figure.

The front section 12 of the carriage 10 essentially includes a plateau 16 whose function is to flatten the cornea in advance of the cutting blade in such a way as to define the thickness of the corneal flap which will be cut by the blade 14.

According to the invention, the ring 1 is equipped with a lug 17 which projects above the plane of the slide 8 in such a way as to constitute an abutment for the front of the flattening plateau 16.

In actual fact, in the embodiment in FIGS. 1 and 2, it is not strictly speaking the front of the plateau which abuts against the lug 17, but an abutment element 18 carried by the plateau 16. In the embodiment represented, this abutment element 18 is in the form of a conical washer placed on a finger 19 integral with the plateau 16, the angle of the cone of the washer 18 and the forward inclination of the finger 19 being such that the front generatrix of the washer 18 is situated in the plane, here vertical, of the lug 17 facing the carriage 10 and protruding in relation to the front of the plateau 16. By placing washers of different diameters on the finger 19, it is possible to limit the travel of the carriage in relation to the ring in the direction of the cut in the cornea at different stages, and this makes it possible to adjust the extent of the cut, hence the extent of the part of the corneal flap remaining attached to the eye.

In a variant which is not shown, the finger 19 can be implanted perpendicular to the plateau 16 of the carriage, and the washer 18 can consist of a strictly cylindrical washer. It is not a departure from the scope of the invention either to provide a kinematic inversion of these abutment elements, that is to say to place on the ring a finger which permits washers or cams of different diameters to be engaged on it in order to constitute different abutments at the front of the plateau 16.

One of the consequences of creating these abutment means is that the plateau 16 does not extend up to the end of the rails 13 of the carriage 10. It will in fact be noted, in particular in FIG. 2, that these rails overshoot the front of the plateau 16 via their end 13a. These arrangements mean it is possible to retain a sufficient guide length, especially when the carriage is introduced inside the slides 8, at the start of the operation of cutting the cornea, without thereby necessitating too great an extension of the dimension of the ring in a direction parallel to the slide 8, which would be an obstacle to positioning this ring on the eye of a patient.

FIG. 3 shows only a securing ring of a keratome according to the invention, in which the abutment element for the carriage which is carried by the ring 1 is in fact a disk 20 mounted rotatably in an eccentric manner on a pivot integral with the ring 1 and capable of being adjusted in angular position around this pivot by means of a maneuvering knob 21a of a pin 21.

In this figure it will be noted that the ring is provided with a maneuvering grip 22 which is shaped as a fork, of which each of the prongs 23 and 24 is implanted in an inclined manner on the upper surface of the ring on each side of the slide face 8. The knob 21a for maneuvering the eccentric disk 20 extends via a pin which passes through the grip 22, the latter forming an element for guiding and supporting this pin. It will be appreciated from this diagram that the front section 12 of the carriage can move freely between the prongs 23, 24 of the grip 22. This grip extends in a direction parallel to that of the slide 8 and affords the surgeon a more ergonomic maneuver of the keratome, since with his left hand he will actuate the carriage in the direction of the arrow A, and with his right hand, for example, he will hold the grip 22 in opposition to the movement A of his left hand. This arrangement of the grip in the axis of the slide 8 will also provide the surgeon with very precise sensitive information when the carriage comes into abutment against the eccentric disk 20. Finally, the prongs 23 and 24 which are inclined toward the outside of the ring 1 leave a large field of vision free above this ring for the surgeon, who proceeds with the cutting.

FIG. 4 is a diagrammatic representation of a ring 1 belonging to the keratome according to the invention, equipped with a grip 22 as described in FIG. 3 and equipped with eye speculum elements 25, 26. These elements are represented in the form of substantially curvilinear troughs oriented parallel to the slide 8 and coupled to the ring, or to the base of each of the prongs 23 and 24 of the fork of the grip 22, via elements 27 and 28 which are represented very schematically. These elements 27 and 28 have the function of holding the troughs 25 and 26 correctly applied against the eyelids in order to spread these open to the maximum and they are therefore elements which act elastically on the troughs 25 and 26 in order to resist the tendency of the eyelids to move toward one another. In addition, the securing elements 27 and 28 can have the possibility of adjusting the level of the troughs 25 and 26 of the eye speculum in relation to the surface of the eye. Since the llustration in FIG. 4 is essentially diagrammatic, any means permitting coupling of the eye speculum to the ring of the keratome according to the invention naturally remains within the scope of the present invention.

In the case where the plateau 16 abuts directly against a cam, such as that in FIGS. 3 and 4, the carriage can advantageously be made of transparent material, which allows the surgeon to monitor precisely the behavior of the cornea during cutting.

We claim:

1. A microkeratome for surgery of the cornea comprising securing ring having an upper face provided with a slide and a blade carriage having a lower face provided with guide means for cooperating with said slide, said blade carriage including a front section forming a plateau for flattening the cornea, wherein said ring is provided with a stop element and said carriage is provided with a stop element abutting said stop element of said ring for limiting the sliding movement of the carriage on said slide of the ring to a given relative position of said carriage and said ring.

2. The microkeratome as claimed in claim 1, wherein the stop element of said ring includes a lug rising above the upper face of said ring.

3. The microkeratome as claimed in claim 2, wherein said plateau of said carriage includes a pin, said stop element of said carriage comprising a washer movably engaged on said pin and projecting out of the plateau towards said stop element of the ring.

4. The microkeratome as claimed in claim 2, wherein said guide means include two lower side rails which project beyond said front section of the carriage.

5. The microkeratome as claimed in claim 1, wherein said stop element of the ring is a cam piece the positions of which relative to the ring being adjustable.

6. The microkeratome as claimed in claim 5, wherein said ring includes a maneuvering grip of the ring in the shape of a fork having two prongs implanted at an inclination in the ring on either side of the slide and wherein said cam piece is integral with a maneuvering pin passing through said grip.

7. The microkeratome as claimed in claim 1, wherein the carriage is made of transparent material.

8. The microkeratome as claimed in claim 1, wherein the ring is equipped on either side of the slide with eye speculum elements.

* * * * *